United States Patent [19]

Merry et al.

[11] Patent Number: 4,929,235
[45] Date of Patent: * May 29, 1990

[54] SELF-SEALING PERCUTANEOUS TUBE INTRODUCER

[75] Inventors: Jack D. Merry, Glens Falls; E. David Fink, Schenectady, both of N.Y.

[73] Assignee: Universal Medical Instrument Corp., Ballston Spa, N.Y.

[*] Notice: The portion of the term of this patent subsequent to Jan. 29, 2004 has been disclaimed.

[21] Appl. No.: 760,817

[22] Filed: Jul. 31, 1985

[51] Int. Cl.$^5$ .................. A61M 5/00; A61M 25/00
[52] U.S. Cl. ................................ 604/167; 604/256; 128/766; 137/849; 251/249.1
[58] Field of Search ............... 604/167, 169, 256, 247; 128/656-658, 766; 137/849; 251/149.1

[56] References Cited

U.S. PATENT DOCUMENTS

| 584,091 | 6/1897 | Leidich | 137/849 |
|---|---|---|---|
| 2,524,764 | 10/1950 | Burke | 137/849 |
| 3,577,992 | 5/1971 | Merry et al. | 604/99 |
| 4,000,739 | 1/1977 | Stevens | 604/167 X |
| 4,424,833 | 1/1984 | Spector et al. | 604/167 X |
| 4,430,081 | 2/1984 | Timmermans | 604/167 X |

*Primary Examiner*—Dalton L. Truluck
*Attorney, Agent, or Firm*—Lackenbach Siegel Marzullo & Aronson

[57] ABSTRACT

A self-sealing percutaneous tube (e.g. catheter) introducer having a sealing mechanism to prevent blood or fluid leakage that includes spaced sealing gaskets adapted to surround the tube, a distal sealing element being planar and having a slit whereas the proximal sealing element being conical and having an annular opening at its distal and small end, the introducer optionally including a side arm flushing member and/or a female luer lock connection at its proximal end.

13 Claims, 1 Drawing Sheet

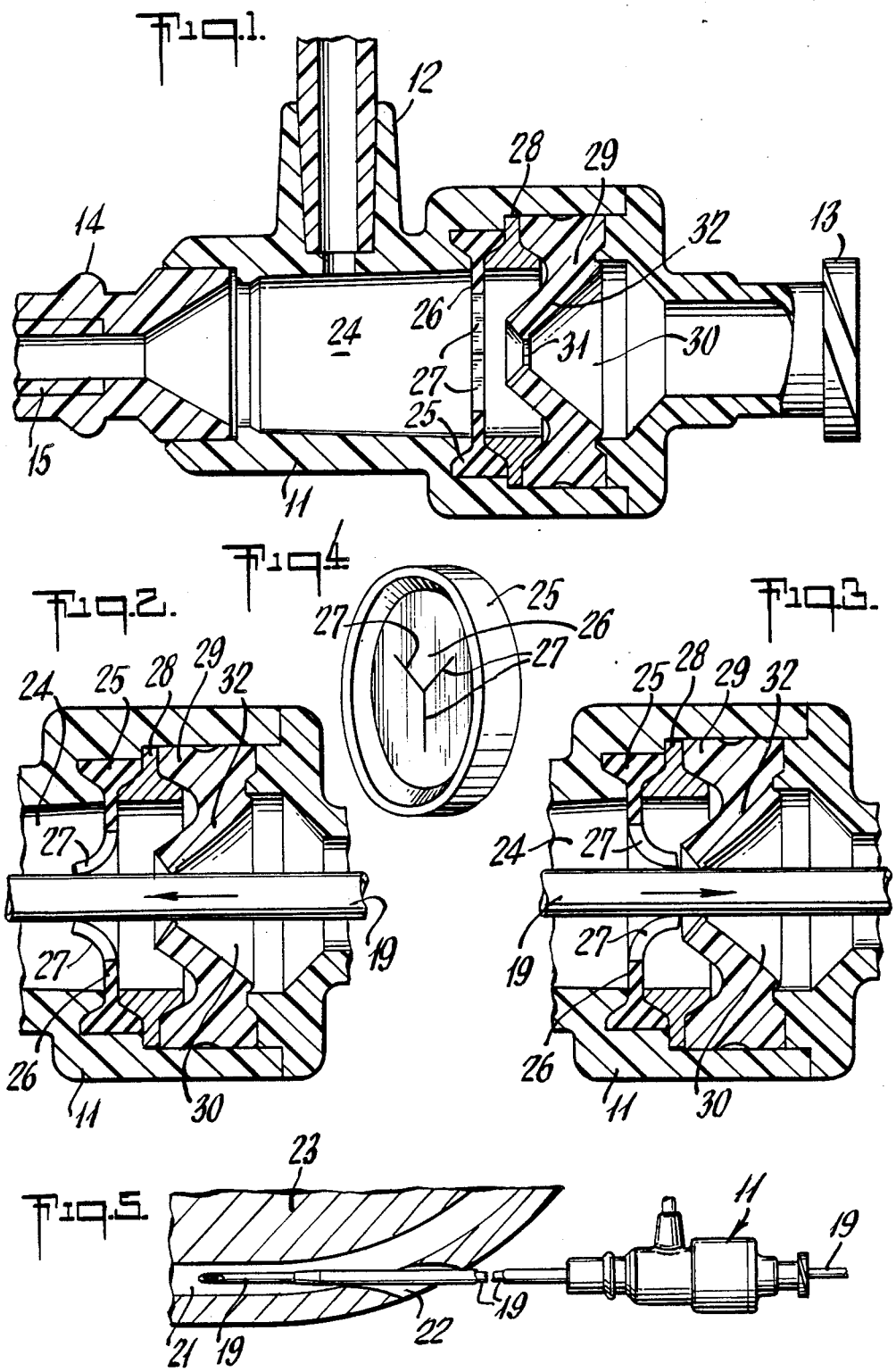

SELF-SEALING PERCUTANEOUS TUBE INTRODUCER

BACKGROUND OF THE INVENTION

This invention relates to new and useful improvements in self-sealing gaskets within cannulas or percutaneous catheter introducers through which tubes such as balloon catheters, electrodes, biopsy instruments, closed-end cardiovascular catheters, etc. may be inserted and removed, and in which the valve-gaskets maintain a seal at all times. Such devices are used in medical procedures where it is often required to insert one tube through another tube or into a housing or vessel while maintaining the outer tube, housing or vessel sealed at all times.

Angiography is a noted and valuable procedure used to diagnose cardiovascular disease. It involves the introduction of a hollow tubular catheter into one of the major arteries or veins, such as the femoral or brachial arteries, and advancing and maneuvering it into smaller branching vessels which are to be studied. After the catheter is in position, a radiopaque fluid is injected through the catheter into the desired area and X-rays taken for diagnostic study.

Techniques for catheter introduction include "cut down" and other modifications of the "Seldinger" technique. The "cut down" technique involves surgically opening a vein or artery and introducing the angiographic catheter directly through the incision.

30 *American Journal of Cardiology*, 378, (September, 1972), describes a modification of the Seldinger technique, wherein a percutaneous sheath is introduced into the lumen of a blood vessel. A hollow needle is inserted through the skin and into the lumen, a guide wire is passed through the needle and advanced up the artery or vein into the organ to be studied. The needle is then removed, leaving the guide wire in the vessel. A sheath and dilator unit are advanced over the wire into the vessel, and, the dilator is removed along with the guide wire. Now, any type of catheter desired of similar diameter, can be inserted through the sheath into the vessel. To avoid excessive bleeding, and to reduce the possibility of an air embolism, this technique and others require the physician to occlude the orifice of the sheath during catheter changes.

These methods are characterized, especially if multiple studies are indicated, by blood clots, blood loss, venous thrombosis, subcutaneous hematomas, and other adverse conditions to patients.

PRIOR ART

Self-sealing cannulas or catheter introducers have been developed for these procedures. These cannulas can be left in the vessel during angiographic or other catheterization while the catheter is freely manipulated within the cannula and vessel, with little or no blood loss. A seal capable of withstanding the patient's blood pressure, when the catheter has been removed, is also provided, thus obviating the necessity of occluding the cannula and preventing significant blood loss at all times.

U.S. Pat. No. 4,000,739 to Stevens discloses a self-sealing gasket arrangement in a catheter introducer that includes a pair of planar slitted and apertured disc gaskets in face-to-face relation at the proximal end of the cannula. The proximal disc has an annular opening and the distal disc has a Y-slit.

U.S. Pat. No. 4,424,833 discloses a one piece self-sealing gasket molded from a resilient latex rubber, having spaced sealing portions wherein the proximal seal has an annular hole and the distal seal has a Y-slit, said seals being spaced by the walls of the unit.

FIELD OF THE INVENTION

The present field is surgical percutaneous introduction of elongated cylindrical devices such as hollow catheters, electrodes, biopsy instruments, closed-end cardiovascular catheters, etc. into blood vessels whereby leakage of blood is prevented through the introducer and optionally providing a side port for blood sampling, infusion, pressure monitoring or aspiration of fibrin deposits or other debris.

SUMMARY OF THE INVENTION

The present invention provides a self-sealing percutaneous tube introducer having a pair of spaced flexible resilient gasket members and optionally a side port. The proximal gasket has an annular opening at the distal and sharp end of a conical projection and the distal seal has a Y-slit, with sufficient space between so that passage distortion of a distally moving tube will not cause the seals to touch (but they may touch on proximal movement of the tube and resultant displacement of the distal seal).

Further objects, advantages and features of the introducer of this invention will be apparent from the following more detailed description and an illustrative embodiment of the invention shown in the accompanying drawings.

BRIEF DESCRIPTION OF THE DRAWINGS

FIG. 1 is a longitudinal cross section of an introducer embodying the invention;

FIG. 2 is a partial cross section through the sealing elements, showing a catheter being moved distally;

FIG. 3 is a similar partial cross section of the sealing elements showing the catheter being moved proximally;

FIG. 4 is a perspective view of the Y-slit gasket, and

FIG. 5 shows a unit positioned within a patient.

DESCRIPTION OF THE PREFERRED EMBODIMENT

The drawings show a main valve body 11 provided with a side port 12, a female luer lock cap 13, a distal lock 14 and a strain relief tube 15 which is attached to the sheath 17. A tube 18 is attached to the side port 12 and leads to a connector or stopcock for infusion, e.g. heparin, flushing, blood sampling, pressure monitoring, etc.

The female luer lock 13 permits easy attachment of items not shown, such as a syringe for quick medication, or infusion, a corrugated sterile sleeve to maintain sterility in the catheter while it is being introduced and removed if desirable, etc.

FIG. 5 shows the unit with a catheter 19 inserted within a vessel lumen 21 through incision 22 of a patient's arm or leg 23, the catheter extending proximally beyond the valve for attachment to a pressure dye source or for manipulation by an operator, etc.

Within the passage flow chamber 24, there is positioned a gasket 26 having a Y-slit 27 and flange 25, a spacer ring 28 and a spaced second gasket 29 provided with a hole 31 that terminates a conical portion 32 that points toward the Y-slit gasket 26. At resting position or during tubular distal movement, the gaskets do not touch. The Y-slit panels only touch the hole gasket during movement of a catheter proximally as shown in FIG. 3. The Y-slit gasket is of sufficient rigidity to maintain the planar position of FIG. 1 against the patient's blood pressure when no catheter is present.

The conical construction of hole gasket 29 helps guide the catheter into the appropriate position when being moved distally but more important, causes little or no destruction or resistance to the movement of the catheter, and particularly balloon catheters which must be handled with care. On proximal movement of catheters (particularly large ones), the conical portion 32 may invert into space 30 proximal to hole gasket 29.

The gaskets are made from silicone rubber or other flexible blood compatible elastomers including natural and synthetic rubbers and pastics. They should have a Shore A durometer of 30 to 80, preferably about 50–60 for the hole gasket and 60–70 for the Y-slit gasket. The spacer ring 28 is metal or hard plastic.

Although Y-slit is preferable, it can be replaced with T, L, X, single straight line, or other type slits.

These self-sealing units are intended to be disposable units, i.e. discarded after a single procedure. However, in a single procedure, it is common to insert and remove several devices, e.g. one catheter may be replaced by another during the procedure, or at a minimum the spring guide and dilator will probably be removed. Thus, the integrity of the seals beyond one sliding tubular member is important.

It has been found that if two gaskets are positioned in abutting relationship or even spaced as part of a single unitary construction, and particularly without the conical arrangement of the hole gasket, the removal of a catheter or other device may invert the entire gasket relationship, which together with inadequate space allowance and/or provision for retention, may result in damage or dislodging of the gaskets or damage to the catheter. This conical design does not jam, permits easier movement of catheter without stress thereon, and allows use of greater variability in catheter sizes in the same unit, apparently because of greater flexibility and possible inversion.

We claim:

1. A self-sealing percutaneous tube introducer comprising a body having a passage therethrough adapted to receive a catheter or similar medical device, a flexible hole gasket mounted transverse to and within said passage having a round hole centered therein, a flexible slit gasket mounted transverse to and within said passage having a slit which permits said catheter to pass through by deflecting or stretching portions of the gasket adjacent said slit, and an inflexible spacing ring mounted between said gaskets, said slit gasket being spaced distally from said hole gasket but close enough that said slit gaskets if moved proximally by said catheter may reach and rest upon the perimeter of said hole, but not interfere with catheter movement.

2. The introducer of claim 1 wherein said slit is Y-shaped.

3. The introducer of claim 2 wherein said hole gasket is conical with the smaller end directed toward the slit gasket.

4. The introducer of claim 3 wherein said hole gasket is spaced from the proximal end of said introducer.

5. The introducer of claim 4 additionally comprising a side arm located distally to said gaskets.

6. The introducer of claim 4 additionally comprising a luer attachment at said proximal end.

7. The introducer of claim 4 additionally comprising a female luer attachment at said proximal end.

8. The introducer of claim 4 wherein said gaskets are formed from blood compatible flexible elastomers.

9. The introducer of claim 8 wherein said spacer ring is metal.

10. The introducer of claim 9 wherein said gaskets are formed from blood compatible silicone rubber.

11. The introducer of claim 10 wherein said gaskets have a Shore A durometer of 30 to 80.

12. The introducer of claim 11 wherein the Shore A durometer of said hole gasket is about 50 to 60 and said slit gasket is about 60 to 70.

13. The introducer of claim 8 wherein said spacer ring is hard plastic.

* * * * *